United States Patent
Mikhajlov et al.

(10) Patent No.: US 10,710,049 B2
(45) Date of Patent: Jul. 14, 2020

(54) METHOD FOR ACTIVATING A CATALYST, REACTOR, AND METHOD OF OBTAINING HYDROCARBONS IN FISCHER-TROPSCH PROCESS

(71) Applicant: ROSNEFT OIL COMPANY (ROSNEFT), Moscow (RU)

(72) Inventors: Mikhail Nikolaevich Mikhajlov, Moscow (RU); Dmitrij Aleksandrovich Grigor'ev, Lobnya (RU); Oleg Nikolaevich Protasov, Klintsy (RU); Nikolaj Aleksandrovich Mamonov, Khimki (RU); Aleksej Eduardovich Bessudnov, Moscow (RU); Pavel Mikhajlovich Stupakov, Klintsy (RU); Aleksandr Vasil'evich Sandin, Ryazan (RU)

(73) Assignee: ROSNEFT OIL COMPANY (ROSNEFT), Moscow (RU)

( * ) Notice: Subject to any disclaimer, the term of this patent is extended or adjusted under 35 U.S.C. 154(b) by 0 days.

(21) Appl. No.: 16/470,191

(22) PCT Filed: Nov. 2, 2017

(86) PCT No.: PCT/RU2017/000812
§ 371 (c)(1),
(2) Date: Oct. 4, 2019

(87) PCT Pub. No.: WO2018/111149
PCT Pub. Date: Jun. 21, 2018

(65) Prior Publication Data
US 2020/0023334 A1    Jan. 23, 2020

(30) Foreign Application Priority Data
Dec. 15, 2016  (RU) ................................. 2016149363

(51) Int. Cl.
*B01J 19/24*    (2006.01)
*C07C 1/04*    (2006.01)
(Continued)

(52) U.S. Cl.
CPC ............... *B01J 19/249* (2013.01); *B01J 8/06* (2013.01); *C07C 1/041* (2013.01); *C07C 1/042* (2013.01);
(Continued)

(58) Field of Classification Search
CPC .. B01J 19/249; B01J 8/06; B01J 2208/00539; B01J 2208/06; B01J 2208/0057;
(Continued)

(56) References Cited

U.S. PATENT DOCUMENTS

| 7,217,741 B2 | 5/2007 | Bowe et al. |
| 9,011,788 B2 | 4/2015 | Hartvigsen et al. |

(Continued)

FOREIGN PATENT DOCUMENTS

| EA | 014214 B1 | 10/2010 |
| EA | 022062 B1 | 10/2015 |

(Continued)

OTHER PUBLICATIONS

International Search Report issued in International Application No. PCT/RU2017/000812, dated Feb. 14, 2018 (Feb. 14, 2018) [English language].

(Continued)

*Primary Examiner* — Jafar F Parsa
(74) *Attorney, Agent, or Firm* — Mintz Levin Cohn Ferris Glovsky and Popeo, P.C.

(57) ABSTRACT

The invention relates to Fischer-Tropsch synthesis in a compact version. A compact reactor comprises a housing, rectangular reaction channels inside the housing, which are filled with a cobalt catalyst, synthesis gas injection nozzles (Continued)

in the number determined by the ratio of the number of channels to the number of synthesis gas injection nozzles, an input and output nozzle for heat transfer medium on which a pressure controller installed, and an assembly for withdrawing synthetic hydrocarbons. The cobalt catalyst is activated by passing hydrogen through it. Synthetic hydrocarbons are produced by passing synthesis gas through the reaction channels filled with the activated cobalt catalyst. The space velocity of synthesis gas is increased every 300-500 h, followed by returning to the initial process conditions. This provides a high-molecular-weight hydrocarbon output per unit mass of the reactor.

5 Claims, 2 Drawing Sheets

(51) Int. Cl.
*B01J 8/06* (2006.01)
*C10G 2/00* (2006.01)
(52) U.S. Cl.
CPC .................. *C10G 2/00* (2013.01); *C10G 2/30* (2013.01); *C10G 2/32* (2013.01); *C10G 2/332* (2013.01); *C10G 2/34* (2013.01); *B01J 2208/00539* (2013.01); *B01J 2208/00557* (2013.01); *B01J 2208/00902* (2013.01); *B01J 2208/06* (2013.01)
(58) Field of Classification Search
CPC ... C10G 2/00; C10G 2/30; C10G 2/32; C10G 2/332; C10G 2/34; C07C 1/042; C07C 1/041
See application file for complete search history.

(56) References Cited

U.S. PATENT DOCUMENTS

| 9,199,215 | B2 | 12/2015 | Hartvigsen et al. |
| 9,359,271 | B2 | 6/2016 | LeViness et al. |
| 2013/0216448 | A1 | 8/2013 | Hartvigsen et al. |
| 2015/0210606 | A1 | 7/2015 | LeViness et al. |

FOREIGN PATENT DOCUMENTS

| KR | 10-2014-0035867 | A | 3/2014 |
| NL | 8006656 | A | 10/1981 |
| RU | 2208475 | C2 | 7/2003 |
| RU | 2445161 | C1 | 3/2012 |
| RU | 2524217 | C2 | 7/2014 |
| RU | 2638217 | C1 | 12/2017 |
| WO | WO-02/083817 | A2 | 10/2002 |
| WO | WO-2004/050799 | A1 | 6/2004 |
| WO | WO-2008/104793 | A2 | 9/2008 |
| WO | WO-2012/054455 | A2 | 4/2012 |
| WO | WO-2018/111149 | A1 | 6/2018 |

OTHER PUBLICATIONS

International Search Report issued in International Application No. PCT/RU2017/000812, dated Feb. 14, 2018 (Feb. 14, 2018) [Russian language].
Written Opinion of the International Searching Authority issued in International Application No. PCT/RU2017/000812, Box No. V, dated Feb. 14, 2018 (Feb. 14, 2018) [English language translation of Box No. V at p. 5].

METHOD FOR ACTIVATING A CATALYST, REACTOR, AND METHOD OF OBTAINING HYDROCARBONS IN FISCHER-TROPSCH PROCESS

TECHNICAL FIELD

The invention relates to the field of oil, gas and coal chemistry and concerns Fischer-Tropsch synthesis, in particular, a reactor for producing synthetic hydrocarbons by a Fischer-Tropsch process and a method for conducting a Fischer-Tropsch synthesis reaction in a compact version.

BACKGROUND

Many companies are working on the implementation of compact mobile technologies for processing natural gas into synthetic hydrocarbons. The main advantage of such technologies is their possibility of use in small and distant hydrocarbon fields. In particular, they are focused on processing associated petroleum gas (APG), a significant part of which is burned off at fields. The Fischer-Tropsch synthesis technology in a compact version will improve the utilization of APG and natural gas in small and distant fields, thus increasing the profitability of their development.

Compact reactor dimensions are driven by the need for transportation of Fischer-Tropsch synthesis plants to distant fields on various types of transport, including by road. To ensure acceptable weight and dimensional characteristics and to reduce capital costs when designing mobile plants for processing hydrocarbon gases into synthetic crude oil, the output per unit mass of the reactor must be of at least 1000 g $C_{5+}/kg_{reactor}$/day, which is usually provided with a catalyst productivity of more than 1000 kg $C_{5+}/m^3_{cat}$·h.

A high productivity rate of the Fischer-Tropsch process in a compact version is usually achieved by using catalysts with a content of cobalt of at least 30%, for example, as described in WO 2008104793 A2, publ. 4 Apr. 2008; EA 014214 B1, publ. 29 Oct. 2010 and others. The catalysts are required to be activated before their use to produce synthetic hydrocarbons. The activation is preferably performed in situ in a compact Fischer-Tropsch synthesis reactor under conditions (temperature, pressure) that are within the range of the working Fischer-Tropsch process conditions.

The stable operation of compact reactors at a high productivity rate for a long time is ensured by keeping the reactors in isothermal mode. Because of a high Fischer-Tropsch reaction thermal effect of 165 kJ/mol, a high activity of used catalysts, and high volumes of processed raw materials, an intensive heat removal is necessary in order to keep the Fischer-Tropsch process at its high productivity rate in the isothermal mode, for which it is expedient to use an endothermic process with a comparable thermal effect, for example the boiling of liquid. Among the available heat transfer media that can be used at temperatures of Fischer-Tropsch synthesis reactions, water is characterized by a maximum value of specific vaporization heat. In addition, the factor of heat transfer from a wall to boiling water is higher than in single-phase water flow. Under boiling, the temperature in the cooling jacket is determined by the pressure and remains constant, strictly ensuring the isothermal mode in reaction channels, and in cooling by fluid flow, the fluid flow, as passes through the reaction channel, heats up, which leads to a decrease in a temperature drop between the wall and the flow, thereby additionally reducing the efficiency of the heat removal, and may cause a disturbance in the isothermal mode in the reactor. Therefore, it is preferable that a reactor for implementation of the method for producing synthetic hydrocarbons in a Fischer-Tropsch process in a compact version allows heat removal due to the boiling of water.

The boiling of water in the cooling jacket can occur in two modes—pool boiling and flow boiling. In the first case, vapor bubbles detached from a heat-dissipating wall and carry the heat to the flow core of heat transfer medium. This generates an additional agitation, which contributes to the flow turbulization and an increase in the factor of heat transfer from the wall. In the second case, generated vapor bubbles move through a narrow channel along the heat-dissipating wall at a speed greater or less than the speed of the liquid phase, depending on the direction of the action of Archimedes force relative to the fluid flow. In this case, as the flow of the flow core of heat transfer medium passes along the heat-dissipating wall, the vapor/liquid ratio increases, which leads to a reduction in the heat transfer factor due to a low thermal conductivity of vapor compared to liquid. The reduction in the heat transfer factor in the case of flow boiling does not allow an effective heat removal along the entire length of the reaction channel and makes it impossible to keep a Fischer-Tropsch synthesis reactor in isothermal mode at its high productivity rates. Therefore, the most effective heat removal required for keeping the Fischer-Tropsch synthesis reactor in the isothermal mode can be ensured under conditions of pool boiling of water in the cooling jacket.

The surface roughness of catalytic channels is also an important parameter for intensification of the boiling process since the generation of bubbles during boiling of heat transfer medium occurs in microscopic cavities. On a smooth surface, the number of places suitable for the emergence of a germinal bubble is limited, so the boiling begins later and is unstable, due to which the same heat flow is achieved at a higher temperature difference between the wall and the core of the flow of heat transfer medium.

A compact reactor for a Fischer-Tropsch synthesis reaction, provided by Compact GTL PLC is known, the reactor consisting of channels in which there is a gas-permeable catalyst structure, as described in U.S. Pat. No. 7,217,741B2, publ. 15 May 2007. The channels of the reactor extend between headers. The construction consists of two reactor units connected in series. The syngas hourly space velocity is in the range 1000-15000 h$^{-1}$ and is selected so that water vapors do not exceed 20 mol. %. To enhance heat transfer and increase the surface area of a catalyst, corrugated foils or metal meshes are used as a substrate for the catalyst within the channels. The catalyst to be used in the proposed reactor for Fischer-Tropsch synthesis is γ-Al$_2$O$_3$ of specific surface area 140-450 m$^2$/g coated with cobalt in an amount of 9-29% by the catalyst weight, wherein ruthenium, platinum or gadolinium oxide is used as a promoter at a Co/promoter ratio of 10000/1 to 10/1. The reactor consists of rectangular plates, each plate being 450 mm long and 150 mm wide and 6 mm thick. Header chambers are welded along each side, each header defining three compartments. Within each of the central compartments of the headers there are coolant tubes that extend the entire height of the reactor. The Fischer-Tropsch process runs in two stages. The reaction gas is cooled between the stages so as to condense water vapors. The conversion of carbon monoxide at the first stage does not exceed 70%. At the second stage, the conversion of the residual CO is not more than 70%. The process temperature is not higher than 210° C. The productivity of a reactor of 8 m in length is 200 barr/day, which corresponds to an output per unit mass of the reactor of 550 g $C_{5+}$/kg$_r$/day in terms of the size of the reaction channels recited in the patent.

Disadvantages of such a reactor and method for conducting a Fischer-Tropsch process in this reactor are the need for a two-stage process, which leads to a low output per unit mass of the reactor; the cooling tubes located only in the central part of the reactor and the heat removal due to the flow of water inside tubes reduce the efficiency of heat removal and may result in difficulties in keeping the reactor in isothermal operation mode. The efficiency of heat removal from the reaction channels cannot be increased by pool boiling of water in the cooling tubes in the reactor of the proposed design.

U.S. Pat. No. 9,011,788 B2, publ. 21 Apr. 2015, discloses a compact reactor unit for Fischer-Tropsch synthesis of Ceramatec Inc., consisting of tubes with aluminum inserts inside them. The insert consists of six radially extending fins contacting with the inner wall of the tube. The fins comprise cross-fins disposed towards the inner surface of the tube. This design of the internal part of the reactor allows effective removal of the heat generated by the Fischer-Tropsch reaction, from the center of the catalytic layer to the reactor walls. The Fischer-Tropsch process in such a reactor is carried out in the presence of a cobalt or iron catalyst dispersed in a microfibrous matrix, at 210-235° C. with a temperature drop inside the tube of not more than 25° C.

A disadvantage of this method is the complexity of the tube design with internal inserts and an increase in the specific quantity of metal of the reactor unit by 1.5 times compared with the classical tubular reactor. In view of the increase in specific quantity of metal, the output per unit mass of the reactor at maximum catalyst productivity of 1875 kg $C_{5+}/m^3_{cat}$·h is 691 g $C_{5+}$/kg$_r$/day. In addition, the maximum temperature drop of 25° C. as indicated can lead to unstable operation of the reactor at a high productivity rate.

U.S. Pat. No. 9,199,215 B2, publ. 1 Dec. 2015, describes a highly efficient reactor provided by Ceramatec Inc., consisting of several cylindrical tubes charged with a catalyst. Each reactor tube is placed within an external pipe, which in turn is housed within the reactor shell. The design of the reactor allows two cooling loops. The primary longitudinal cooling loop passes in external pipes. Thus, the heat generated by the Fischer-Tropsch reaction is transferred to the wall of the pipes. The fluid in the second cooling loop flows within the shell and across the outside of the pipes. The flow of heat transfer medium in the second cooling loop is perpendicular to the flow in the primary loop. Internal baffles divide the reactor shell into a plurality of chambers. The use of baffles makes it possible to regulate the number and direction of flows in the second loop, thereby changing the intensity of cooling. The Fischer-Tropsch process in such a reactor also runs in the presence of a cobalt or iron catalyst dispersed in a microfibrous matrix, at a temperature of 210-235° C.

A disadvantage of this invention is the need to use an additional external pipes and internal baffles to obtain a two loop cooling system, which leads to an increases in the specific quantity of metal more than 2.4 times and an increased size of the reactor and reduces the output per unit mass of the reactor to less than 650 g $C_{5+}$/kg$_r$/day. The pool-boiling mode for water, which is maximally effective for heat removal from the reaction tubes, cannot be reached in a narrow gap between the reaction tubes and the external pipes of the primary cooling loop.

The closest technical solution to the present invention is a compact reactor (microchannel unit) provided by Velocys Inc. and a method for conducting a Fischer-Tropsch reaction using said reactor, as described in U.S. Pat. No. 9,359,271 B2, publ. 7 Jun. 2016. The microchannel units are made in the form of cubic blocks with a length of 10 meters and consist of repeating units comprising reaction channels filled with a catalyst, and cooling channels filled with water. Water is fed to the cooling channels orthogonally to the feed flow in the reaction channels. Each synthesis microchannel may have a cross section having any shape, for example, a square, rectangle, circle, or semi-circle. The thicknesses of the channels may be up to 10 mm, and the length may be up to 10 m. The microchannels for heat transfer also may have any shape having a thickness of up to 2 mm, a width of up to 3 m, and a length of up to 10 m. The Fischer-Tropsch synthesis process in this reactor is conducted, according to the presented examples, in the presence of cobalt-containing catalysts based on a silica support modified with 16 wt. % $TiO_2$, promoted by 0.05 wt. % Re, wherein the content of cobalt ranges from 18 to 43 wt. %. The catalyst is to be pre-activated at a temperature of from 300 to 600° C. and under a pressure of from 0.1 to 10 MPa for 2-24 hours in a reducing gas medium, wherein the reducing gas can be hydrogen, gaseous hydrocarbons and their mixtures, as well as a mixture of hydrogen and nitrogen, or synthesis gas. The process of producing high-molecular hydrocarbons in the microchannel reactor in the presence of the activated catalyst is carried out using synthesis gas at an $H_2$/CO ratio of 1.4 to 2.1, a space velocity of at least 1000 h$^{-1}$, a temperature of 150-300° C., and a pressure of no more than 5.0 MPa. According to the examples, the productivity of the claimed catalyst in the microchannel reactor is 680-1530 kg/m$^3_{cat}$·h.

A disadvantage of this reactor is inefficient removal of the reaction heat by the flow of heat transfer medium through the cooling channels. The inefficiency of heat removal in the reactor of such a design is evidenced by a high content of nitrogen in synthesis gas, which is 16.5-35.0 vol. %, since the feedstock is usually diluted with nitrogen to prevent overheating in the catalyst bed. The intensity of heat removal is adjusted by changing the flow rate of heat transfer medium and the size of the cooling channels, which does not allow keeping the reactor in isothermal operation mode and reduces productivity due to local overheating of the catalyst bed and the corresponding decrease in the catalyst selectivity for high molecular weight hydrocarbons. The efficiency of heat removal due to boiling water in the cooling channels in a reactor of this design can be increased only in the "flow boiling" mode, which is characterized by less efficient heat removal because the generated vapor bubbles cannot leave the near-wall region, as is done in the "pool boiling" mode. This does not allow an effective production of synthetic hydrocarbons in a compact reactor of the above-indicated design. Another disadvantage of this method is the pre-activation at a temperature of 300-600° C., which is higher than the temperature of the synthesis of hydrocarbons by the Fischer-Tropsch method, which is in the range of 150 to 300° C. The activation in situ in a Fischer-Tropsch synthesis reactor requires a more expensive refractory steels. In addition, the pre-activation of a catalyst at a temperature of above 300° C. makes it impossible to ensure the isothermal mode of the reactor, which will lead to uneven regeneration of the catalyst along the length of the catalyst bed and to its unstable operation in Fischer-Tropsch synthesis of hydrocarbons, as well as to a low catalyst productivity. The activation in a separate reactor (ex situ) is fraught with technological difficulties associated with the transportation of the activated catalyst to a Fischer-Tropsch reactor and with the use of additional equipment, which also contradicts the condition of compactness of the claimed method of Fischer-Tropsch synthesis.

Another disadvantage of the proposed reactor design and the method of Fischer-Tropsch synthesis in such a reactor is an increased specific quantity of metal per the structure, which reduces the daily output per unit mass of the reactor. For example, for a reactor consisting of five reaction channels and six heat removal channels with channel sizes of both types of 56×50×2 mm and a wall thickness of 2 mm, the daily productivity of the reactor in accordance with the productivity specified in the examples can be in the range of 457 to 1028 g $C_{5+}$/day. In this case, the approximate mass of the reactor will be at least 1.2 kg, which corresponds to a daily output per unit mass of the reactor of 380 to 857 g $C_{5+}/kg_r$·day.

The technical problem of the claimed group of inventions consists in developing a compact reactor for the production of synthetic hydrocarbons in a Fischer-Tropsch process, a method for activating a cobalt catalyst, and implementing the Fischer-Tropsch process to produce synthetic hydrocarbons in the compact reactor with a high yield of synthetic hydrocarbons.

SUMMARY OF THE INVENTION

The technical result provided by the claimed group of inventions is to achieve high-molecular-weight hydrocarbon output per unit mass of the reactor of at least 1160 g $C_{5+}/kg_r$/day at a productivity of a Fischer-Tropsch synthesis catalyst of at least 1200 kg $C_{5+}/m^3{}_{cat}$·h and a CO conversion of at least 69%.

THE BEST EMBODIMENT OF THE INVENTION

The technical result is achieved by a reactor for the production of synthetic hydrocarbons in a Fischer-Tropsch process, comprising a housing with channels filled with a cobalt catalyst, wherein the channels have a thickness of from 1 to 5 mm and a rectangular cross section; synthesis gas injection nozzles; input and output nozzles for heat transfer medium; and an assembly for withdrawing synthetic hydrocarbons, characterized in that a pressure controller is installed on the output nozzle for heat transfer medium, the outer surface of the wall of the reaction channels with the catalyst has a roughness of 1.6 to 25 µm, a distance between the nearest reaction channels is 1 to 5 mm, the wall thickness of the reaction channel is 1 to 3 mm, the width-to-thickness ratio of the reaction channel is 2 to 100, and the height-to-thickness ratio of the reaction channel is from 20 to 2000, wherein the ratio of the number of reaction channels to the number of synthesis gas injection nozzles is from 1 to 50. The ratio of the total cross-sectional area of the reaction channels to the cross-sectional area of the housing is from 0.17 to 0.89 to ensure the boiling of water in the "pool boiling" mode.

In addition, the technical result is achieved by that a cobalt Fischer-Tropsch catalyst suitable for conducting a Fischer-Tropsch process in a compact version in a compact reactor for the production of synthetic hydrocarbons in the Fischer-Tropsch process is activated by passing hydrogen through the reaction channels filled with the catalyst with a space velocity of 1000-30000 $h^{-1}$ at a temperature of 200-280° C. and a pressure of 0.1-3.0 MPa for 1-48 h. The process is conducted in the presence of a cobalt catalyst, and the Fischer-Tropsch process for the production of synthetic hydrocarbons is conducted in a compact reactor by feeding synthesis gas to the reaction channels of the compact reactor filled with the activated cobalt catalyst at an $H_2$/CO ratio of from 2.22 to 2.60, a space velocity of 10000 to 19000 $h^{-1}$, a temperature of 210-260° C., and a pressure of 1.0-3.0 MPa, wherein every 300-500 hours the space velocity of the synthesis gas is increased up to 20000-30000 $h^{-1}$ by 1-5 hours, followed by returning to the initial conditions of the process.

These features are essential.

A reactor of the described structure, when used in the method of producing synthetic hydrocarbons in a Fischer-Tropsch process in a compact version provides, at a CO conversion of at least 69%, a catalyst productivity in terms of high-molecular-weight hydrocarbons of at least 1200 kg/$m^3{}_{cat}$·h and an output per unit mass of the reactor of at least 11600 g $C_{5+}/kg_r$/day.

Under boiling, the temperature in the cooling jacket is determined by the pressure and remains constant, strictly ensuring an isothermal mode in the reaction channels.

Figure 1:
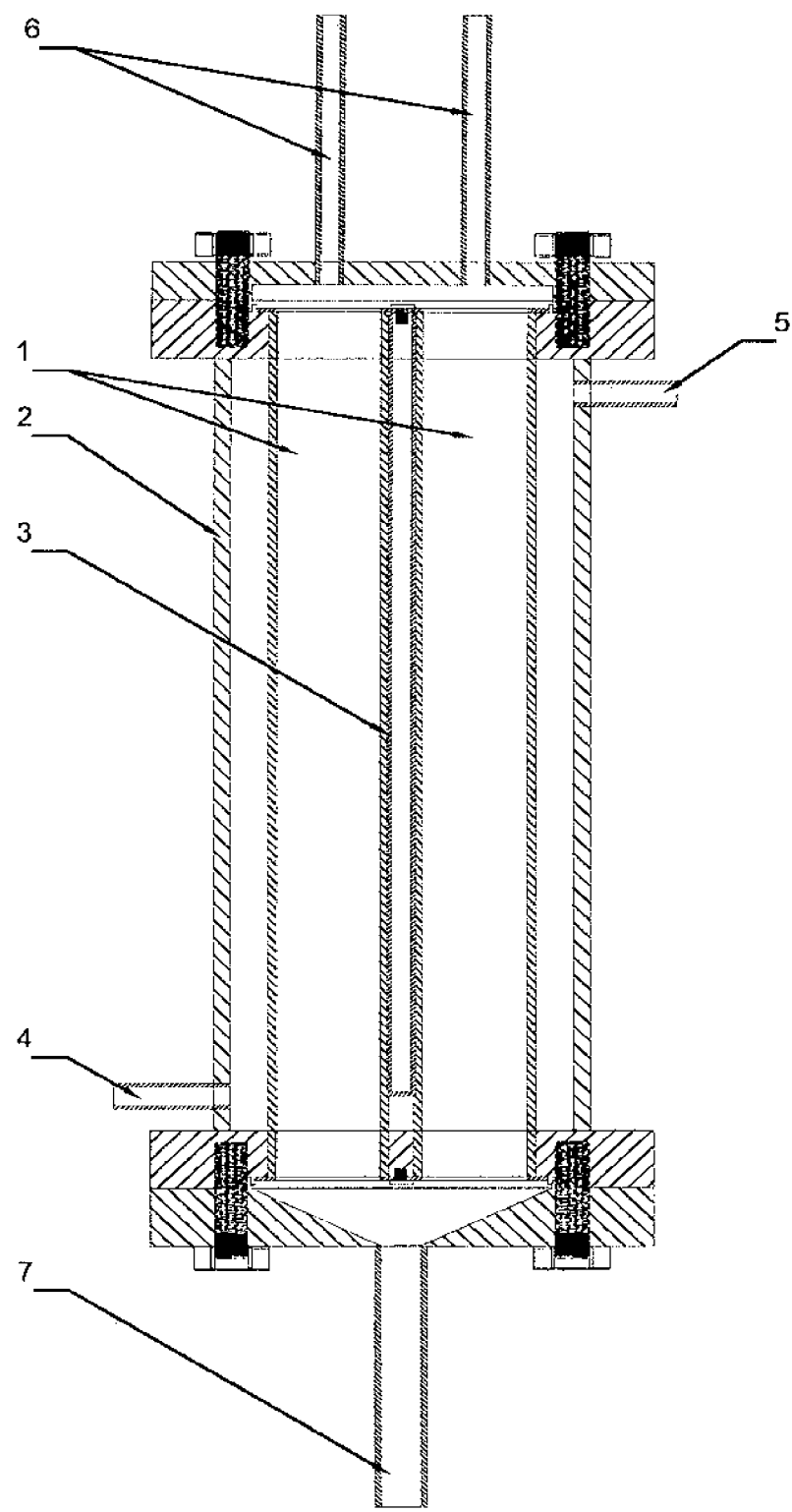
FIG. 1 shows a longitudinal section of the reactor.
Figure 2:
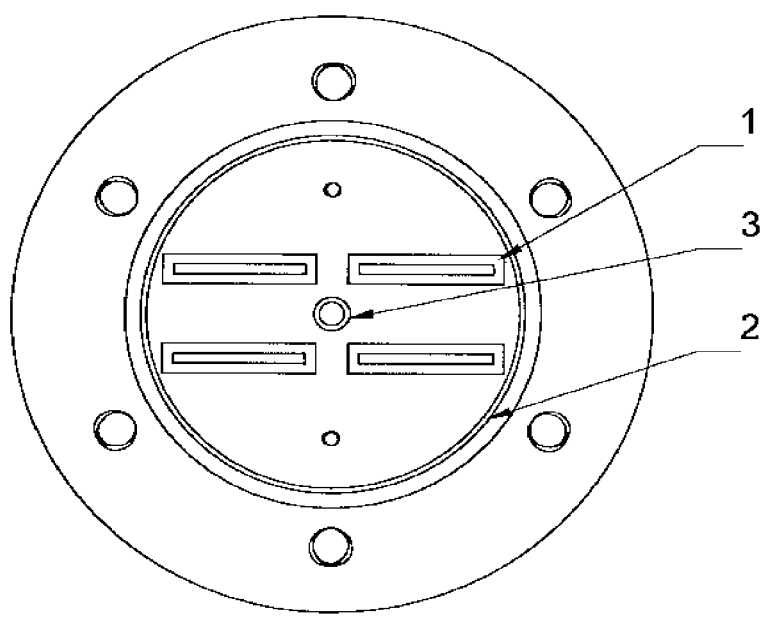
FIG. 2 shows an end view of the reactor.

The reactor consists of rectangular minichannels (1) having a thickness of 1 to 5 mm and a width-to-thickness ratio of from 2 to 100, and a height-to-thickness ratio of from 20 to 2000. The thickness of the wall of the reaction channels is from 1 to 3 mm. The outer surface of the channels with a catalyst has a roughness of 1.6 to 25 µm. The reaction channels are placed in a housing (2) having a cross section of any shape, for example, round, rectangular, square. The ratio of the total cross-sectional area of the channels to the cross-sectional area of the housing is from 0.17 to 0.89 to ensure the boiling of water in the "pool boiling" mode. The temperature profile in the cooling jacket of the catalytic zone of the reactor is controlled by thermocouples placed in a thermocouple channel (3) disposed between the reaction channels in the cooling jacket coaxially with the central axis of the reactor. The isothermal mode of the Fischer-Tropsch process in the reaction channels is maintained by boiling water in the cooling jacket in the "pool boiling" mode. The temperature is determined by the pressure of water in the jacket and remains constant, strictly ensuring the isothermal mode in the reaction channels. Water is fed into the reactor-cooling jacket through an input nozzle (4) and discharged through an output nozzle (5), on which a pressure controller (not shown) is installed to control the pressure of water in the jacket. A uniform flow distribution of feedstock through the channels is provided by several injection nozzles (6), a number of which is determined by the ratio of a number of channels to a number of nozzles in the range from 1 to 50. Products are withdrawn through a withdrawal nozzle (7). Reaction minichannels (1) are evenly spaced in the tubular space of the cooling jacket relative to the central axis of the reactor with a distance between the nearest channels of from 1 to 5 mm, for example, as shown in FIG. 2. At the ends, the body of the cooling jacket is closed by flanges.

For use of the reactor according to the present invention in a method for producing synthetic hydrocarbons in a Fischer-Tropsch process in a compact version, a cobalt catalyst is loaded into the reaction minichannels for conducting the Fisher-Tropsch process in a compact version. The cobalt catalyst is pre-activated in situ in the Fischer-Tropsch synthesis reactor in a hydrogen stream at a space velocity of 1000-30000 $h^{-1}$, a temperature of 200-280° C., and a pressure of 0.1-3.0 MPa.

The production of synthetic hydrocarbons in the Fischer-Tropsch process in a compact version in the minichannel compact reactor according to the present invention is carried out in the presence of an in situ activated cobalt catalyst for Fischer-Tropsch synthesis, which is suitable for the use in a compact version at its maximum productivity rate under conditions selected from the following ranges: an $H_2/CO$ ratio of 2.22 to 2.60, a temperature of 210-260° C., a pressure of 1.0-3.0 MPa, and a synthesis gas feed space velocity of 10000-20000 $h^{-1}$. When the method for producing synthetic hydrocarbons is carried out in a compact version, the process is performed under conditions of the maximum productivity, according to which, every 300-500 hours, the space velocity is increased up to 20000-30000 $h^{-1}$ by 1-5 h at the temperature, pressure, and $H_2/CO$ ratio, which correspond to the conditions of maximum productivity, followed by returning to the initial conditions of the synthesis.

The maximum performance conditions mean herein a combination of the temperature, pressure, space velocity, and $H_2/CO$ ratio in synthesis gas, which provides the maximum productivity of the designed reactor after activation in the developed activation mode at a catalyst productivity of more than 1200 kg $C_{5+}/m^3_{cat}\cdot h$ and a conversion of CO of at least 69%.

The operating efficiency of the compact minichannel reactor is evaluated on the results of the study of characteristics of a cobalt catalyst when a Fischer-Tropsch process is carried out at a high productivity rate.

The CO conversion is calculated according to the following equation:

$$K_{CO} = \frac{m_{CO}^{in} - m_{CO}^{out}}{m_{CO}^{in}} \cdot 100\%,$$

wherein $m_{CO}^{in}$ is the weight of carbon monoxide in 1 $m^3$ of gas injected into the reactor;

$m_{CO}^{out}$ is the weight of carbon monoxide in 1 $m^3$ of gas discharging from the reactor.

The selectivity for liquid hydrocarbons is calculated according to the following equation:

$$S_{C_{5+}} = \frac{\frac{m_C}{C_{5+}}}{\frac{m_C}{CO_{in}} - \frac{m_C}{CO_{out}}} \cdot 100\%,$$

wherein $$\frac{m_C}{C_{5+}}$$

is the weight of carbon contained in liquid hydrocarbons resulting from the synthesis in time τ;

$$\frac{m_C}{CO_{in}}$$

is the weight of carbon contained in carbon monoxide injected into the reactor in time τ;

$$\frac{m_C}{CO_{out}}$$

is the weight of carbon contained in carbon monoxide discharging from the reactor in time τ.

The catalyst productivity is calculated according to the following equation:

$$P_{cat} = \frac{m_{C_{5+}}}{t \cdot V_{out}},$$

wherein $m_{C_{5+}}$ is the weight of high molecular weight hydrocarbons resulting from Fischer-Tropsch synthesis for time τ, kg;

τ is the duration of the synthesis, h;

$V_{cat}$ is the volume of the catalyst loaded into the Fischer-Tropsch synthesis reactor, $m^3$.

The output per unit mass of the reactor is calculated according to the following equation:

$$P_r = \frac{P_{cat} \cdot V_{cat} \cdot 24 \cdot 1000}{m_r},$$

wherein $m^r$ is the weight of the Fischer-Tropsch synthesis reactor, kg.

The content of the initial and resulting substances in the gases escaping from the Fischer-Tropsch synthesis reactor can be determined by any known method, for example, by gas chromatography.

EMBODIMENTS OF THE INVENTION

The Fischer-Tropsch process in a compact version can be performed in accordance with the following examples.

EXAMPLE 1

The structure of a compact reactor for the production of synthetic hydrocarbons in a Fischer-Tropsch process includes a housing containing four reaction channels filled with a cobalt catalyst containing 44.0 wt. % Co and 56.0 wt. % $ZrO_2$; wherein the reaction channels has a thickness of 4 mm, a width-to-thickness ratio of 10, and a height-to-thickness ratio of 2000 and are placed in an outer housing sealed with two flange connections. The thickness of the wall of the reaction channel is 1.5 mm. The distance between the nearest reaction channels is 3 mm. The ratio of the total cross-sectional area of the channels to the cross-sectional area of the housing is 0.17. To obtain a uniform flow distribution of feedstock, the ratio of the number of channels to the number of synthesis gas injection nozzles is 2. A pressure controller is installed on an output nozzle. The outer surface of the channels with a catalyst has a roughness of 25 μm.

The cobalt catalyst consisting of 44.0 wt. % Co and 56.0 wt. % $ZrO_2$, filling the reaction channels of the compact reactor is activated by passing hydrogen with a space velocity of 5000 $h^{-1}$ at a temperature of 250° C. and a pressure of 1.9 MPa for 28 hours.

The Fischer-Tropsch process for the production of synthetic hydrocarbons in the compact reactor runs at an $H_2/CO$ ratio in synthesis gas of 2.37, a synthesis gas feed space velocity of 10000 h$^{-1}$, a temperature of 210° C. and a pressure of 2.0 MPa. In addition, every 350 hours the synthesis gas space velocity is increased up to 20000 h$^{-1}$ by 3 hours, followed by returning to the initial conditions of the synthesis.

The composition of synthetic hydrocarbons resulting from the Fischer-Tropsch process in a compact version in the reactor according to the invention is as follows:
54 wt. % of $C_5$-$C_{10}$ hydrocarbons;
39 wt. % of $C_{11}$-$C_{18}$ hydrocarbons; and
7 wt. % of $C_{19+}$ hydrocarbons.

Characteristics of the reactor and cobalt catalyst obtained in the method of producing synthetic hydrocarbons in the Fischer-Tropsch process in a compact version in the reactor according to the invention are given in the table below.

EXAMPLE 2

The structure of a compact reactor for the production of synthetic hydrocarbons in a Fischer-Tropsch process includes a housing containing 50 reaction channels filled with a cobalt catalyst containing 46.0 wt. % Co, 13.5 wt. % $ZrO_2$, and 40.5 wt. % $SiO_2$; wherein the reaction channels has a thickness of 1 mm, a width-to-thickness ratio of 2, and a height-to-thickness ratio of 400 and are placed in an outer housing sealed with two flange connections. The thickness of the wall of the reaction channel is 1 mm. The distance between the nearest reaction channels is 1 mm. The ratio of the total cross-sectional area of the channels to the cross-sectional area of the housing is 0.89. To obtain a uniform flow distribution of feedstock, the ratio of the number of channels to the number of synthesis gas injection nozzles is 50. A pressure controller is installed on an output nozzle. The outer surface of the channels with a catalyst has a roughness of 11 μm.

The catalyst consisting of 46.0 wt. % Co, 13.5 wt. % $ZrO_2$, and 40.5 wt. % of $SiO_2$, filling the reaction channels of the compact reactor is activated by passing hydrogen with a space velocity of 1000 h$^{-1}$ at a temperature of 280° C. and a pressure of 3.0 MPa for 48 hours.

The Fischer-Tropsch process for the production of synthetic hydrocarbons in the compact reactor runs at an $H_2$/CO ratio in synthesis gas of 2.12, a synthesis gas feed space velocity of 15000 h$^{-1}$, a temperature of 250° C. and a pressure of 1.0 MPa. In addition, every 300 hours the synthesis gas space velocity is increased up to 30000 h$^{-1}$ by 5 hours, followed by returning to the initial conditions of the synthesis.

The composition of synthetic hydrocarbons resulting from the Fischer-Tropsch process in a compact version in the reactor according to the invention is as follows:
62 wt. % of $C_5$-$C_{10}$ hydrocarbons;
33 wt. % of $C_{11}$-$C_{18}$ hydrocarbons; and
5 wt. % of $C_{19+}$ hydrocarbons.

Characteristics of the reactor and cobalt catalyst obtained in the method of producing synthetic hydrocarbons in the Fischer-Tropsch process in a compact version in the reactor according to the invention are given in the table below.

EXAMPLE 3

The structure of a compact reactor for the production of synthetic hydrocarbons in a Fischer-Tropsch process includes a housing containing eight reaction channels filled with a cobalt catalyst containing 48.0 wt. % Co, 2.0 wt. % Re, and 50.0 wt. % $ZrO_2$; wherein the reaction channels has a thickness of 5 mm, a width-to-thickness ratio of 100, and a height-to-thickness ratio of 1000 and are placed in an outer housing sealed with two flange connections. The thickness of the wall of said reaction channel is 3 mm. The distance between the nearest reaction channels is 5 mm. The ratio of the total cross-sectional area of the channels to the cross-sectional area of the housing is 0.38. To obtain a uniform flow distribution of feedstock, the ratio of the number of channels to the number of synthesis gas injection nozzles is 1. A pressure controller is installed on an output nozzle. The outer surface of the channels with a catalyst has a roughness of 1.6 μm.

The cobalt catalyst consisting of 48.0 wt. % Co, 2.0 wt. % Re, and 50.0 wt. % $ZrO_2$, filling the reaction channels of the compact reactor is activated by passing hydrogen with a space velocity of 30000 h$^{-1}$ at a temperature of 200° C. and a pressure of 1.2 MPa for 12 hours.

The Fischer-Tropsch process for the production of synthetic hydrocarbons in the compact reactor runs at an $H_2$/CO ratio in synthesis gas of 2.60, a synthesis gas feed space velocity of 19000 h$^{-1}$, a temperature of 260° C., and a pressure of 3.0 MPa. In addition, every 500 hours the synthesis gas space velocity is increased up to 25000 h$^{-1}$ by 1 hour, followed by returning to the initial conditions of the synthesis.

The composition of synthetic hydrocarbons resulting from the Fischer-Tropsch process in a compact version in the reactor according to the invention is as follows:
64 wt. % of $C_5$-$C_{10}$ hydrocarbons;
32 wt. % of $C_{11}$-$C_{18}$ hydrocarbons; and
4 wt. % of $C_{109+}$ hydrocarbons.

Characteristics of the reactor and catalyst obtained in the method of producing synthetic hydrocarbons in Fischer-Tropsch process in a compact version in the reactor according to the invention are given in the table below.

EXAMPLE 4

The structure of a compact reactor for the production of synthetic hydrocarbons in a Fischer-Tropsch process includes a housing containing 12 reaction channels filled with a cobalt catalyst containing 50.0 wt. % Co, 0.5 wt. % Ru, 19.8 wt. % $Al_2O_3$, and 29.7 wt. % $SiO_2$; wherein the reaction channels has a thickness of 3 mm, a width-to-thickness ratio of 5, and a height-to-thickness ratio of 20 and are placed in an outer housing sealed with two flange connections. The thickness of the wall of said reaction channel is 2 mm. The distance between the nearest reaction channels is 4 mm. The ratio of the total cross-sectional area of the channels to the cross-sectional area of the housing is 0.52. To obtain a uniform flow distribution of feedstock, the ratio of the number of channels to the number of synthesis gas injection nozzles is 4. A pressure controller is installed on an output nozzle. The outer surface of the channels with a catalyst has a roughness of 17 μm.

The cobalt catalyst consisting of 50.0 wt. % Co, 0.5 wt. % Ru, 19.8 wt. % $Al_2O_3$, and 29.7 wt. % $SiO_2$, filling the reaction channels of the compact reactor is activated by passing hydrogen with a space velocity of 30000 h$^{-1}$ at an $H_2$/CO ratio in synthesis gas of 2.52, a synthesis gas feed space velocity of 13000 h$^{-1}$, a temperature of 240° C., and a pressure of 2.0 MPa. In addition, every 400 hours the synthesis gas space velocity is increased up to 28000 h$^{-1}$ by 2 hours, followed by returning to the initial conditions of the synthesis.

The composition of synthetic hydrocarbons resulting from the Fischer-Tropsch process in a compact version in the reactor according to the invention is as follows:

60 wt. % of $C_5$-$C_{10}$ hydrocarbons;
33 wt. % of $C_{11}$-$C_{18}$ hydrocarbons; and
7 wt. % of $C_{19+}$ hydrocarbons.

Characteristics of the reactor and catalyst obtained with the method of producing synthetic hydrocarbons in the Fischer-Tropsch process in a compact version in the reactor according to the invention are given in the table below.

TABLE

Characteristics of the Fischer-Tropsch process

| Example | CO conversion, % | C5+ selectivity, % | Catalyst productivity, kg $C_{5+}$/m³$_{cat}$/h | Output per unit mass of the reactor, g $C_{5+}$/kg$_r$/day |
|---|---|---|---|---|
| 1 | 70.2 | 70.2 | 1212.7 | 1163.5 |
| 2 | 70.7 | 66.3 | 1432.6 | 1375.3 |
| 3 | 69.9 | 61.0 | 1673.3 | 1606.8 |
| 4 | 69.8 | 68.3 | 1348.4 | 1294.7 |

The design of a compact reactor for the production of synthetic hydrocarbons in a Fischer-Tropsch process, a method for activating a Fischer-Tropsch catalyst, and a method for Fischer-Tropsch synthesis in a compact version using the compact reactor, implemented according to the present invention ensure the production of synthetic hydrocarbons in the Fischer-Tropsch process in the compact reactor at a cobalt catalyst productivity of more than 1200 kg/m³$_{cat}$·h and daily output per unit mass of the reactor of more than 1160 g $C_{5+}$/kg$_r$/day, suggesting that the claimed group of inventions is useful for the Fischer-Tropsch process in the compact reactor directly at the fields for highly effective utilization of APG and natural gas.

The design of a compact reactor for the production of synthetic hydrocarbons in a Fischer-Tropsch process, a method for activating a cobalt Fischer-Tropsch catalyst, and the method for the Fischer-Tropsch synthesis in a compact version using the compact reactor, according to the invention, are more efficient than those known in the art.

The invention claimed is:

1. A compact reactor for the production of synthetic hydrocarbons in a Fischer-Tropsch process, comprising a housing with reaction channels filled with a cobalt catalyst, wherein the channels have a thickness of 1 to 5 mm and a rectangular cross section; synthesis gas injection nozzles; input and output nozzles for heat transfer medium; and an assembly for withdrawing synthetic hydrocarbons, wherein the reactor is characterized in that a pressure controller is installed on the output nozzle for heat transfer medium, the outer surface of the wall of the reaction channels with the catalyst has a roughness of 1.6 to 25 μm, a distance between the nearest reaction channels is 1 to 5 mm, a thickness of the wall of the reaction channel is 1 to 3 mm, a width-to-thickness ratio of the reaction channel is 2 to 100, and a height-to-thickness ratio of the reaction channel is from 20 to 2000, wherein a ratio of the number of reaction channels to the number of synthesis gas injection nozzles is from 1 to 50.

2. The reactor according to claim 1, characterized in that a ratio of the total cross-sectional area of the reaction channels to the cross-sectional area of the housing is from 0.17 to 0.89 to provide the boiling of water in a "pool boiling" mode.

3. A method for activating a catalyst in the compact reactor for the production of synthetic hydrocarbons in Fischer-Tropsch process according to claim 1, characterized in that hydrogen is passed through the reaction channels filled with the cobalt catalyst at a space velocity of 1000 to 30000 h$^{-1}$, a temperature of 200 to 280° C., and a pressure of 0.1 to 3.0 MPa for 1 to 48 h.

4. A method of carrying out a Fischer-Tropsch process to produce synthetic hydrocarbons in the compact reactor, characterized in that synthesis gas with an H$_2$/CO ratio of 2.22 to 2.60 is fed at a space velocity of 10000 to 19000 h$^{-1}$ to reaction channels of the compact reactor filled with the cobalt catalyst activated according to the method of claim 3, wherein every 300-500 hours the synthesis gas space velocity is increased up to 20000-30000 h$^{-1}$ by 1-5 h, followed by returning to the initial conditions of the process.

5. The method according to claim 4, characterized in that the Fischer-Tropsch process is carried out at a temperature of 210-260° C. and a pressure of 1.0 to 3.0 MPa.

* * * * *